United States Patent [19]

Mantovani et al.

[11] Patent Number: 5,210,294
[45] Date of Patent: May 11, 1993

[54] PROCESS FOR THE PRODUCTION OF PURIFIED LACTIC ACID AQUEOUS SOLUTIONS STARTING FROM FERMENTATION BROTHS

[75] Inventors: Giorgio Mantovani, Ferrara; Giuseppe Vaccari, Stienta; Anna L. Campi, Ferrara, all of Italy

[73] Assignee: Himont Incorporated, Wilmington, Del.

[21] Appl. No.: 893,179

[22] Filed: Jun. 3, 1992

[30] Foreign Application Priority Data

Jun. 6, 1991 [IT] Italy ............................ 91 A 001555

[51] Int. Cl.$^5$ ...................... C07C 51/42; C07C 59/08
[52] U.S. Cl. ................................. 562/580; 562/515; 562/589
[58] Field of Search ........................ 562/515, 580, 589

[56] References Cited

U.S. PATENT DOCUMENTS 2,664,441 12/1953 Owens et al. ...................... 562/580
4,444,881 4/1984 Urbas ................................. 562/589
5,068,418 11/1991 Kulprathipanja et al. .......... 562/589

FOREIGN PATENT DOCUMENTS 0868926 5/1961 United Kingdom ................ 562/580

OTHER PUBLICATIONS

Montgomery, "The Chemical Production of Lactic Acid from Sugars," Sugar Research Foundation, Inc., pp. 7–8 (1949).
Holten et al., "Lactic Acid: Properties and Chemistry of Lactic Acid and Derivatives," Verlag Chemie, pp. 176–181 (1971).

Primary Examiner—José G. Dees
Assistant Examiner—B. Frazier

[57] ABSTRACT

Purified lactic acid aqueous solutions obtained by percolating fermentation broths through columns of appropriate ion-exchange resins.

13 Claims, No Drawings

PROCESS FOR THE PRODUCTION OF PURIFIED LACTIC ACID AQUEOUS SOLUTIONS STARTING FROM FERMENTATION BROTHS

The present invention concerns a process for the production of purified aqueous lactic acid solutions starting from fermentation broths.

Lactic acid is a product which finds application in a variety of fields; it can be added to food products, for example, or used in the chemical and pharmaceutical field. In particular, an increasingly interesting application is the use of lactic acid as monomer for the synthesis of biodegradable homopolymers and copolymers.

As a matter of fact, there is a growing demand for biodegradable polymers, both as replacements for generically used conventional plastic materials, and for new and specific uses, such as the gradual release of medication within the human or animal organisms, the manufacture of bioabsorbable prostheses, or the controlled release of pest-control substances in agriculture. One of the ways by which lactic acid can be produced industrially is to ferment carbohydrate in an aqueous environment using appropriate bacteria bases (lactobacilli).

Depending on the bacteria basis used one can obtain $L(+)$ or $D(-)$ lactic acid, or racemic acid.

The product resulting from the above mentioned fermentation is made up of a broth containing, besides the lactic acid, various substances in solution, and optionally in suspension, in particular non-fermented carbohydrates, fermentation by-products, and nutrients used for the culture of the bacteria. Moreover, the above mentioned broth contains variable quantities of cells deriving from the culture of the bacteria used for the fermentation. Therefore, in order to obtain the purest possible aqueous lactic acid solution, optionally concentrated, it is necessary to purify the lactic acid present in the fermentation broth depending on the use that said solution is destined for.

For example, for the preparation of lactic acid polymers it is advantageous use aqueous solutions of lactic acid at about 90% by weight.

Obviously, the degree of purity of the aqueous solution of lactic acid is also a factor in determining its possible use, and, consequently, its merits.

Moreover, for industrial use it is also necessary that the purification, and optionally the concentration process of the lactic acid aqueous solution be as simple and as economical as possible.

It is also preferable that the above mentioned process allow one to operate in continuous manner, and to recycle the cells and the fermentation broth after the lactic acid has been recovered, thus minimizing environmental problems. Accordingly, the present invention provides a process for the production of purified lactic acid aqueous solutions starting from fermentation broths containing lactic acid, said process comprising the following steps:

A) percolation of the fermentation broth, free of cells, through one or more columns of a strongly anionic ion-exchange resin in the carbonate form;

B) elution of the lactic acid from the column, or columns, mentioned in (A), by way of an aqueous solution of ammonium carbonate;

C) removal of the ammonium carbonate from the solution obtained from the elution mentioned in (B) by way of heating;

D) percolation of the solution obtained in step (C) through one or more columns of a strongly cationic ion-exchange resin in the hydrogen form.

In order to obtain, for step (A), a cell-free fermentation broth, one can use known techniques for the separation of solids in suspension, such as filtration or centrifugation. The cells recovered can be recycled in part to the fermentation vessel, and in part used as biomass.

Preferably, the fermentation broth is prepared by using the smallest possible amount of nutrients for the bacterial culture, thus allowing one to obtain the maximum production of lactic acid.

The strongly anionic ion-exchange resin used in step (A) is selected from the resins known in the art which are capable of fixing the lactate ion.

In general, said resins are obtained starting from partially cross-linked polymer matrixes prepared by way of polymerization of styrene monomers, such as styrene, ethylvinylbenzene, vinyltoluene and methylstyrene; or from ethylene monomers such as acrylic and methacrylic acid esters, acryl and methacrylamides, and from cross-linkable monomers such as divinylbenzene and divinyltoluene. The above mentioned polymer matrixes are then functionalized generally by way of reactions which are capable of grafting amine or cycloamine groups on the polymer chains.

For example, one of the routes commonly followed for the functionalization of polymer matrixes includes the chloroalkylation of styrene-divinylbenzene resins, followed by amination of the chloroalkylized polymer. The amine groups are then salified in order to obtain the ion-exchange effect.

Methods for the preparation of the above mentioned anionic resins are described for example in U.S. Pat. No. 4,224,415.

Therefore all strongly anionic resins are suitable for use according to the process of the present invention, particularly the ones mentioned above, as long as they are in the form of the carbonate, i.e., salified with carbonated anion, and they are capable of fixing the lactate ion and provide it almost completely in the elution with ammonium carbonate carried out in step (B).

Preferred are the resins containing quaternary ammonium groups salified with carbonate anion.

Obviously, in order to be used for this invention, the above mentioned resins are located in one or more columns, with adequate structures and dimensions, depending on the plant in which they are included.

The fermentation broth (where the lactic acid is partially present in the form of lactates, given the need to maintain the bacterial culture at a pH which is not too acid) is allowed to percolate through the above mentioned columns.

The solution exiting the columns can be recycled to the fermentation vessel after a possible addition of carbohydrates and nutrients.

When the capability of the anionic resin to fix the ion lactate goes below acceptable limits, for example below 30% by weight, the column, or columns, of lactate enriched resin are subjected to the elution step (B), optionally preceded by one or more washings with water.

Therefore, in order to carry out continuously the process of the present invention, one must carry out the steps (A) and (B) in at least two interchangeable columns, by alternating the column (columns) wherein are carried out respectively the percolation step (A) and the elution step (B). Similarly, in order to carry out continuously the process of the present invention one must carry out the step (D) and the regeneration step (which follows step (D) and is described below) in at least two interchangeable columns, by alternating the column (columns) wherein are carried out respectively the percolation step (D) and the regeneration step.

Anyhow, the above interchange is not at all burdensome, and, as already mentioned, has the considerable advantage of allowing a continuous operation.

For elution step (B), an aqueous solution of ammonium carbonate is percolated through a column, or columns, of anionic resin containing lactate ion.

Besides eluting the lactate ion in the form of ammonium lactate, said ammonium carbonate solution restores the carbonate form of the anionic resin, thus avoiding operating in two distinct steps for elution and restoration of the carbonate form, with the added advantage of simplifying the process.

The concentration and optimal quantity of the ammonium carbonate solution are selected according to the type of anionic resin used and the specific operating conditions; as a way of example, the concentration of ammonium carbonate in the solution is from 3 to 10% by weight, and preferably, the solution is used in quantities from 1 to 5 volumes per volume of anionic resin per hour. The operation is carried out in ammonium carbonate in excess compared to the lactate set on the resin.

After the above mentioned elution step, and optionally after one or more washings with water, the column or columns of anionic resin are ready to be used again in step (A).

After a given number of cycles it may be best to regenerate the anionic resin with a strong base (NaOH for example) in order to eliminate possible traces of strong anions coming from the fermentation broth which are set on the resin and are not eluted by the ammonium carbonate.

After regeneration, the anionic resin is brought back to the carbonate form, for example by percolating in it an excess of ammonium carbonate in aqueous solution.

The solution obtained from elution step (B) contains ammonium lactate and ammonium carbonate (used in excess, as previously stated) and is then subjected to a treatment which allows the elimination of the ammonium carbonate [step (C)].

For this purpose, and this constitutes one of the advantages of the present invention, one can simply heat the solution, thus obtaining the decomposition of the ammonium carbonate in $CO_2$ and $NH_3$, which are easily removed in gaseous form and can be recovered as ammonium carbonate.

It is possible to operate at the solution boiling temperature, with the added advantage of being able to preconcentrate the solution before step (D) by way of distillation of part of the water.

The product obtained from the step (C) described above, therefore, is made up of a highly pure solution of ammonium lactate.

With the purpose of converting the ammonium lactate in lactic acid, said solution is allowed to percolate through one or more columns of strongly cationic ion-exchange resin, in the hydrogen form [step (D)].

The strongly cationic resin used in step (D) is selected from the resins known in the art, which are capable of fixing the ammonium ion.

Generally, said resins are prepared in the same manner as described for the strong anionic resins used in step (A), except that different functional groups are grafted on the polymer chains.

As previously stated, for the purpose of this invention said functional groups must be in the hydrogen form, i.e., capable of exchanging $H^+$ cations.

Preferred strongly cationic resins which can be conveniently used in the process of the present invention are, for example, cationic resins containing sulfonic groups, particularly of the types described above.

Methods for the preparation of these types of resins are described in the above mentioned U.S. Pat. No. 4,224,415.

The solution obtained from step (D), therefore, is a highly pure lactic acid aqueous solution which can be concentrated by simply evaporating part of the water until the desired concentration is reached.

Obviously the cationic resin used in step (D) become progressively enriched with ammonium ions, and, therefore, as previously stated, must be periodically regenerated.

To this purpose one can use aqueous solutions of a strong acid, such as HCl in a 5% aqueous solution, with a flow velocity of 1.5-2 volumes per volume of resin per hour.

By using, as previously mentioned, two or more interchangeable columns, it is possible to carry out the process of the present invention in continuous, i e., without interrupting the transformation step of the ammonium lactate into lactic acid.

The following example is given in order to illustrate, and not limit, the present invention.

EXAMPLE

A broth obtained by fermentation of glucose in aqueous solution has been treated with *lactobacillus casei* DSM 20011, where the lactic acid concentration varied from 8 to 10% by weight.

The fermentation conditions were as follows:
pH: 6.4-6.6 (neutralization with NaOH 8 N)
temperature: 37° C.
anaerobic conditions
moderate stirring
maximum glucose concentration: 10% by weight
concentration of nutrients in the broth (by weight):
  yeast extract 3%
  magnesium sulfate 0.06%
  ferrous sulfate 0.003%
  manganese sulfate 0.003%
  sodium acetate 0.1%
  biacid potassium phosphate 0.05%
  monoacid potassium phosphate 0.05%.

The above mentioned fermentation broth, after the cells have been separated by way of microfiltration, was percolated through an IRA-420 anionic resin column marketed by Rohm and Haas Italia S.r.l., in the form of carbonate, and comprising a styrene-divinylbenzene resin containing quaternary ammonium groups.

The volume of broth treated was 1 volume/volume of resin, maintaining a flow of 3 volumes per volume of resin per hour.

At the beginning of the treatment the lactic acid was fixed at 100%, while at the end of the treatment the quantity of lactic acid which was fixed equaled to about 30% by weight.

After washing the column with water by reverse flow (3 volumes/volume of resin), the lactic acid was eluted using a solution of ammonium carbonate at 5% by weight of the carbonate in a quantity equal to 3 volumes/volume of resin, and maintaining a flow of 3 volumes per volume of resin per hour.

The eluting solution was heated to about 90° C. and maintained at that temperature until all the ammonium carbonate was eliminated, and it was then percolated through an IR-120 cationic resin column marketed by Rohm and Haas Italia S.r.l. in the hydrogen form, and comprising a styrene-divinylbenzene resin containing sulfonic groups (the volume of the solution treated was about 3 times the volume of the cationic resin).

The eluting lactic acid solution, practically free of impurities, was then concentrated, by distilling part of the water, to about 90% by weight of lactic acid.

Other features, advantages and embodiments of the invention disclosed herein will be readily apparent to those exercising ordinary skill after reading the foregoing disclosure.

In this regard, while specific embodiments of the invention have been described in considerable detail, variations and modifications of these embodiments can be effected without departing from the spirit and scope of the invention as described and claimed.

We claim:

1. A process for the production of purified lactic acid aqueous solutions starting from fermentation broths following steps:
   A) percolation of the fermentation broth, free of cells, through one or more columns of a strongly anionic ion-exchange resin, in the carbonate form;
   B) elution of the lactic acid from the column, or columns, mentioned in (A), by way of an aqueous solution of ammonium carbonate;
   C) removal of the ammonium carbonate from the solution obtained from the elution mentioned in (B) by way of heating;
   D) percolation of the solution obtained in step (C) through one or more columns of a strongly cationic ion-exchange resin, in the hydrogen form.

2. The process of claim 1, where the step (A) and the step (B) are carried out in at least two interchangeable columns, by alternating the columns in which are carried out respectively the step (A) and the step (B).

3. The process of claim 1, where the column or columns used in step (D) are subsequently subjected to a regeneration step using an acid aqueous solution.

4. The process of claim 3, where the step (D) and the regeneration step are carried out in at least two interchangeable columns, by alternating the columns in which are carried out respectively the step (D) and the regeneration step.

5. The process of claim 1, where the strongly anionic resin is a resin containing quaternary ammonium groups.

6. The process of claim 1, where the strong cationic resin is selected from resins containing sulfonic groups.

7. The process of claim 1, where the ammonium carbonate solution used in step (B) contains from about to 10% b weight of ammonium carbonate.

8. The process of claim 2, where the ammonium carbonate solution used in step (B) contains from about 3 to 10% by weight of ammonium carbonate.

9. The process of claim 3, where the ammonium carbonate solution used in step (B) contains from about 3 to 10% by weight of ammonium carbonate.

10. The process of claim 4, where the ammonium carbonate solution used in step (B) contains from about 3 to 10% by weight of ammonium carbonate.

11. The process of claim 5, where the ammonium carbonate solution used in step (B) contains from about 3 to 10% by weight of ammonium carbonate.

12. The process of claim 6, where the ammonium carbonate solution used in step (B) contains from about 3 to 10% by weight of ammonium carbonate.

13. The process of claim 1, where the purified lactic acid aqueous solution is concentrated after step (D) by partial evaporation of the water.

* * * * *

UNITED STATES PATENT AND TRADEMARK OFFICE
CERTIFICATE OF CORRECTION

PATENT NO. : 5,210,294
DATED : May 11, 1993
INVENTOR(S) : Giorgio Mantovani et al.

It is certified that error appears in the above-identified patent and that said Letters Patent is hereby corrected as shown below:

At col. 6, lines 19 and 20, change "from about to 10% b weight" to

--from about 3 to 10% by weight--.

Signed and Sealed this

Fifteenth Day of March, 1994

Attest:

BRUCE LEHMAN

Attesting Officer

Commissioner of Patents and Trademarks